US011045376B2

(12) United States Patent
Yano et al.

(10) Patent No.: US 11,045,376 B2
(45) Date of Patent: Jun. 29, 2021

(54) ROBOTIC OPERATING TABLE

(71) Applicants: MEDICAROID CORPORATION, Kobe (JP); KAWASAKI JUKOGYO KABUSHIKI KAISHA, Hyogo (JP)

(72) Inventors: Yutaro Yano, Kobe (JP); Yoshiyuki Tamura, Kobe (JP); Yukihiko Kitano, Kobe (JP); Mitsuichi Hiratsuka, Kobe (JP); Hiroaki Kitatsuji, Kobe (JP)

(73) Assignees: MEDICAROID CORPORATION, Kobe (JP); KAWASAKI JUKOGYO KABUSHIKI KAISHA, Kobe (JP)

( * ) Notice: Subject to any disclaimer, the term of this patent is extended or adjusted under 35 U.S.C. 154(b) by 363 days.

(21) Appl. No.: 15/906,256

(22) Filed: Feb. 27, 2018

(65) Prior Publication Data

US 2018/0243150 A1    Aug. 30, 2018

(30) Foreign Application Priority Data

Feb. 28, 2017    (JP) .............................. JP2017-035682

(51) Int. Cl.
*A61G 13/04*    (2006.01)
*A61G 13/06*    (2006.01)
(Continued)

(52) U.S. Cl.
CPC ............ *A61G 13/04* (2013.01); *A61B 6/0407* (2013.01); *A61B 6/0487* (2020.08); *A61B 34/30* (2016.02); *A61G 13/06* (2013.01); *A61G 13/104* (2013.01); *A61B 5/0036* (2018.08); *A61B 5/055* (2013.01); *A61B 6/4441* (2013.01);
(Continued)

(58) Field of Classification Search
CPC ...... A61G 13/04; A61G 13/104; A61G 13/06; A61G 2203/12; A61G 2203/20; A61G 2203/42; A61G 2203/14; A61G 2210/05; A61B 34/30; A61B 6/0407; A61B 6/0457;
(Continued)

(56) References Cited

U.S. PATENT DOCUMENTS 7,669,261 B2    3/2010    Fruh et al.
7,860,550 B2    12/2010   Saracen et al.
(Continued)

FOREIGN PATENT DOCUMENTS

| EP | 1028684 B1 | 3/2004 |
| JP | 2014-100301 A | 6/2014 |
| JP | 2016-054860 A | 4/2016 |

*Primary Examiner* — Jeff A Burke
*Assistant Examiner* — Kyle T Johnson
(74) *Attorney, Agent, or Firm* — Metrolex IP Law Group, PLLC (57) ABSTRACT

A robotic operating table according to one or more embodiments may include: a table on which to place a patient; a robotic arm including a plurality of joints, and including a first end supported on a base fixed to a floor, and a second end supporting the table; an operation device including: a move operation receiving unit that receives, from a user, a move operation to move the table, and a register operation receiving unit that receives, from a user, a register operation to register a position of a movement destination of the table and a movement-destination set operation; a memory; and a controller that causes the robotic arm to move the table based on the move operation received by the move operation receiving unit.

22 Claims, 6 Drawing Sheets

(51) Int. Cl.
*A61B 6/04* (2006.01)
*A61B 34/30* (2016.01)
*A61B 6/00* (2006.01)
*A61B 5/00* (2006.01)
*A61G 13/10* (2006.01)
*A61B 5/055* (2006.01)

(52) U.S. Cl.
CPC ...... *A61G 2203/12* (2013.01); *A61G 2203/14* (2013.01); *A61G 2203/20* (2013.01); *A61G 2203/42* (2013.01); *A61G 2210/50* (2013.01)

(58) Field of Classification Search
CPC .... A61B 5/0036; A61B 6/4441; A61B 5/0555

See application file for complete search history.

(56) References Cited

U.S. PATENT DOCUMENTS

| | | | |
|---|---|---|---|
| 8,126,114 B2 | 2/2012 | Naylor et al. | |
| 8,160,205 B2 | 4/2012 | Saracen et al. | |
| 9,326,907 B2 | 5/2016 | Marie | |
| 2005/0166413 A1* | 8/2005 | Crampton | B25J 13/088 33/503 |
| 2007/0101500 A1* | 5/2007 | Fruh | A61G 13/08 5/613 |
| 2009/0003532 A1* | 1/2009 | Weber | A61B 6/0457 378/209 |
| 2010/0237257 A1* | 9/2010 | Saracen | A61N 5/1049 250/491.1 |
| 2011/0187875 A1* | 8/2011 | Sanchez | A61B 34/30 348/207.11 |
| 2012/0035462 A1* | 2/2012 | Maurer, Jr. | A61B 6/5247 600/411 |
| 2015/0000038 A1 | 1/2015 | Obi | |
| 2018/0243150 A1* | 8/2018 | Yano | A61G 13/06 |
| 2018/0325610 A1* | 11/2018 | Cameron | A61B 5/1079 |

* cited by examiner

ROBOTIC OPERATING TABLE

CROSS REFERENCE TO RELATED APPLICATIONS

This application claims priority from prior Japanese Patent Application No. 2017-035682 filed with the Japan Patent Office on Feb. 28, 2017, entitled "ROBOTIC OPERATING TABLE", the entire contents of which are incorporated herein by reference.

BACKGROUND

The disclosure relates to a robotic operating table and a hybrid operation room system.

Japanese Patent Application Publication No. 2014-100301 discloses a hybrid operation room system including a combination of a radiographic fluoroscopic imaging apparatus and an operating table. In Japanese Patent Application Publication No. 2014-100301, the operating table includes a movable top panel on which to place a subject (patient) and a base supporting the movable top panel. The movable top panel of the operating table is slidable in parallel to horizontal directions along the base, which is fixed to the floor. Also, the base of the operating table is freely extendable and contractible in the vertical direction and capable of raising and lowering the movable top panel in the vertical direction.

However, problems with an operating table as described in Japanese Patent Application Publication No. 2014-100301 are that the range of horizontal movement of the movable top panel is small and the freedom of movement of the movable top panel is poor as well. Thus, with such an operating table, it is difficult to move the movable top panel to various positions (patient receiving position, anesthetization position, surgical operation position, imaging position, and so on) desired by medical persons such as surgeons, assistants, nurses, and medical technicians, and it is also difficult to leave sufficient space around the positions at which the medical persons stand due to the small range of movement of the movable top panel. These make it difficult to perform surgery smoothly.

For this reason, there has been a demand from medical persons for an operating table in which a top panel (table) with a patient placed thereon can be moved in a larger range than in the operating table described above. Further, there has also been a demand for an operating table capable of moving a top panel (table) with a patient placed thereon back to a position at which the top panel (table) was positioned a little while ago with a simple operation during treatment or surgery on the patient.

SUMMARY

One or more embodiments may provide a robotic operating table and a hybrid operation room system capable of achieving a large range and freedom of movement of a table on which a patient can be placed, and also capable of moving the table with a patient placed thereon back to a position at which the table was positioned a little while ago with a simple operation.

A robotic operating table according to one or more embodiments may include: a table on which to place a patient; a robotic arm including a plurality of joints, and having a first end supported on a base fixed to a floor, and a second end supporting the table; an operation device including: a move operation receiving unit that receives, from a user, a move operation to move the table, and a register operation receiving unit that receives, from a user, a register operation to register a position of a movement destination of the table and a movement-destination set operation; a memory; and a controller that causes the robotic arm to move the table based on the move operation received by the move operation receiving unit. When the register operation receiving unit receives the register operation in a condition in which the table is placed at a predetermined position, the controller may cause the predetermined position to be stored as a registered position in the memory and may cause a posture of the robotic arm for the table at the predetermined position to be stored in the memory. When the move operation receiving unit receives the move operation in a condition in which the registered position is set as the movement destination of the table, the controller may cause the robotic arm to place the table at the registered position with the posture stored in the memory.

A robotic operating table according to one or more embodiments may include: a table on which to place a patient; a robotic arm including a plurality of joints, and having a first end supported on a base fixed to a floor, and a second end supporting the table; an operation device that receives operations from a user; a memory; and a controller causes the robotic arm to move the table based on a move operation received by the operation device. When the operation device receives a register operation in a condition in which the table is placed at a predetermined position, the controller may cause the predetermined position to be stored as a registered position in the memory and may cause a posture of the robotic arm for the table at the predetermined position to be stored in the memory. When the operation device receives the move operation to move the table to the registered position, the controller may cause the robotic arm to place the table at the registered position with the posture stored in the memory.

A hybrid operation system according to one or more embodiments may include: a robotic operating table; and at least one of a radiographic imaging apparatus configured to capture a radiographic projection image of a patient and a magnetic resonance imaging apparatus configured to capture a magnetic resonance image of a patient. The robotic operating table may include: a table on which to place a patient; a robotic arm including a plurality of joints, and having a first end supported on a base fixed to a floor, and a second end supporting the table; an operation device that receives an operation from a user; a memory; and a controller that causes the robotic arm to move the table based on a move operation received by the operation device. When the operation device receives a register operation in a condition in which the table is placed at a predetermined position, the controller may cause the predetermined position to be stored as a registered position in the memory and may cause a posture of the robotic arm for the table at the predetermined position to be stored in the memory. When the operation device receives the move operation to move to the table to the registered position, the controller may cause the robotic arm to place the table at the registered position with the posture stored in the memory.

DETAILED DESCRIPTION

Embodiments are described with reference to drawings, in which the same constituents are designated by the same reference numerals and duplicate explanation concerning the same constituents may be omitted for brevity and ease of explanation. The drawings are illustrative and exemplary in nature and provided to facilitate understanding of the illustrated embodiments and may not be exhaustive or limiting. Dimensions or proportions in the drawings may not be to scale, and are not intended to impose restrictions on the disclosed embodiments. For this reason, specific dimensions and the like should be interpreted with the accompanying descriptions taken into consideration. In addition, the drawings may include parts whose dimensional relationship and ratios are different from one drawing to another.

Prepositions, such as "on", "over" and "above" may be defined with respect to a surface, for example a layer surface, regardless of the orientation of the surface in space.

One or more embodiments are explained below with reference to drawings.

(Configuration of Robotic Operating Table)

The configuration of a robotic operating table 100 according to one or more embodiments is explained with reference to FIG. 1 to FIG. 6.

Figure 1:
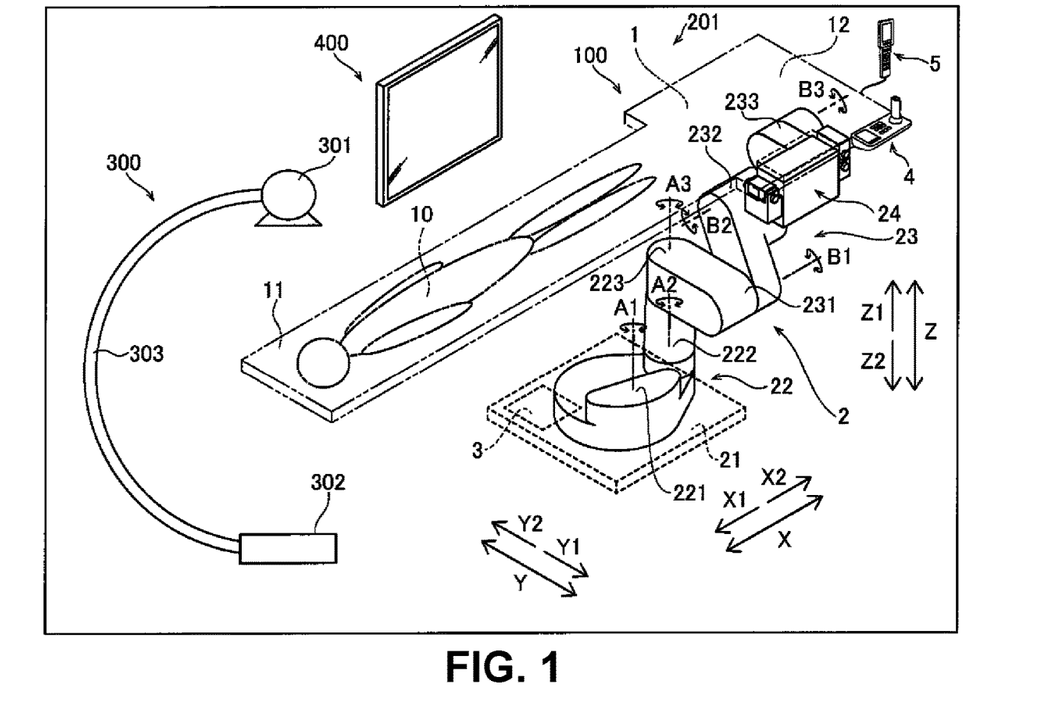
FIG. 1 is a view illustrating an overview of an operating room including a robotic operating table according to one or more embodiments.

As illustrated in FIG. 1, the robotic operating table 100 is provided in an operating room 200. A radiographic imaging apparatus 300 that captures a radiographic projection image of a patient 10 is provided in the operating room 200. The operating room 200 is a hybrid operating room. In other words, a hybrid operation room system 201 including the robotic operating table 100 and the radiographic imaging apparatus 300 is provided in the operating room 200. Also, a display 400 that displays information on surgery is provided in the operating room 200. The display 400 is suspended from an arm (not illustrated), for example, and is movable inside the operating room 200.

The robotic operating table 100 is used as an operating table for operations performed in a setting such as a surgery or internal medicine setting. The robotic operating table 100 is capable of moving a table 1 to a placement position for placing the patient 10 onto the table 1. Also, the robotic operating table 100 is capable of moving the patient 10 to a patient receiving position, an anesthetization position, a surgical operation position, an examination position, a treatment position, a radiographic imaging position, a patient passing position, and so on by moving the table 1 while the patient 10 is placed on the table 1. Also, the robotic operating table 100 is capable of tilting the patient 10 by tilting the table 1 while the patient 10 is placed on the table 1.

The robotic operating table 100 includes the table 1, on which to place the patient 10, an articulated robotic arm 2 (hereinafter, the robotic arm 2), a controller 3, an operation device 4, and an operation device 5.

Figure 2:
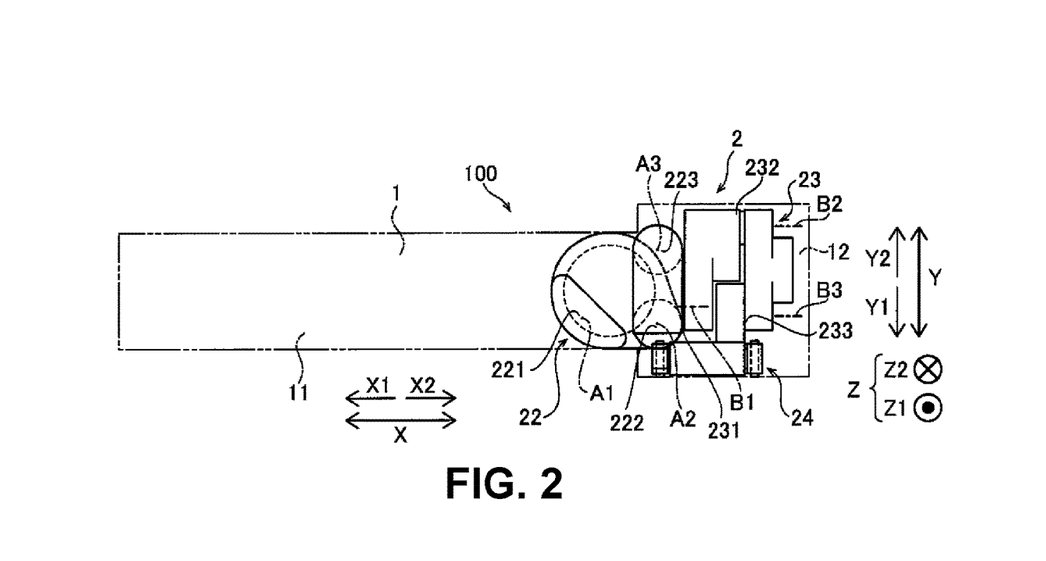
FIG. 2 is a plan view illustrating a robotic operating table according to one or more embodiments.

As illustrated in FIG. 1 and FIG. 2, the table 1 is formed in the shape of a substantially rectangular flat plate. Also, the upper surface of the table 1 is formed to be substantially flat. Note that, while the table 1 is rotatable about an axis extending in the vertical direction (Z direction), the horizontal direction along the longitudinal direction of the table 1 is defined as the X direction and the horizontal direction along the transverse direction of the table 1 is defined as the Y direction in one or more embodiments. In other words, the X direction and the Y direction represent directions based on the table 10.

The table 1 includes a radiolucent part 11 and a support part 12 supporting the radiolucent part 11.

The patient 10 is placed on the radiolucent part 11 of the table 1. The radiolucent part 11 is disposed on the X1 direction side of the table 1. The radiolucent part 11 is formed in a substantially rectangular shape. The radiolucent part 11 is made of a radiolucent material. The radiolucent part 11 is made of a carbon material (graphite), for example. The radiolucent part 11 is made of a carbon fiber reinforced plastic (CFRP), for example. In this way, an image of the patient 10 can be captured using X rays while the patient 10 is placed on the radiolucent part 11.

The support part 12 of the table 1 is connected to the robotic arm 2. The support part 12 is disposed on the X2 direction side of the table 1. The support part 12 is formed in a substantially rectangular shape. The support part 12 supports the radiolucent part 11. The support part 12 is made of a material smaller in radiolucency than the material the radiolucent part 11 is made of. The support part 12 is made of metal, for example. The support part 12 is made of a steel material or an aluminum material, for example.

The table 1 is moved by the robotic arm 2. Specifically, the table 1 is movable in the X direction, which is a horizontal direction, in the Y direction, which is a horizontal direction perpendicular to the X direction, and in the Z direction, which is perpendicular to the X direction and the Y direction and is the vertical direction. Moreover, the table 1 is rotatable (capable of being caused to roll) about an axis extending in the X direction. The table 1 is also rotatable (capable of being caused to pitch) about an axis extending in the Y direction. The table 1 is also rotatable (capable of being caused to yaw) about an axis extending in the Z direction.

The robotic arm 2 moves the table 1. One end of the robotic arm 2 is supported on a base 21 fixed to the floor, while the opposite end supports the table 1. Specifically, the one end of the robotic arm 2 is supported on the base 21 to be rotatable about a base rotation axis (rotation axis A1) extending in the vertical direction (Z direction). The base 21 is a base buried in and fixed to the floor. The base 21 is provided substantially at the center of the range of movement of the table 1 in a plan view (as seen from the Z direction). Also, the opposite end of the robotic arm 2 supports the table 1 at a position near its one end in the longitudinal direction of the table 1 (X direction). Specifically, the opposite end of the robotic arm 2 supports the support part 12, which is disposed on the one end side of the table 1 in the longitudinal direction of the table 1.

The robotic arm 2 is capable of being disposed in such a posture as to be entirely hidden under the table 1 (Z2 direction side) in a plan view (as seen from the Z1 direction). For example, the robotic arm 2 is housed in a housing space which is a space under the table 1 when the table 1 is positioned at the surgical operation position. Specifically, the robotic arm 2 is capable of being disposed in such a posture as to be folded and completely hidden under the table 1 in the plan view (as seen from the Z1 direction) in a state where the robotic arm 2 has moved the table 1 to a position for performing a surgical operation or treatment on the patient 10 placed on the table 1. Meanwhile, the length of the robotic arm 2 in the folded posture in the direction parallel to the longitudinal direction of the table 1 is equal to or shorter than ½ of the length of the table 1 in the longitudinal direction of the table 1.

The robotic arm 2 includes a horizontal articulated assembly 22, a vertical articulated assembly 23, and a pitch mechanism 24. The horizontal articulated assembly 22 includes horizontal joints 221, 222, and 223. The vertical articulated assembly 23 includes vertical joints 231, 232, and 233. Note that the horizontal joints 221 to 223 and the vertical joints 231 to 233 are an example of the "joints" in one or more recited embodiments.

The robotic arm 2 is capable of moving the table 1 with seven degrees of freedom. Specifically, with the horizontal articulated assembly 22, the robotic arm 2 has three degrees of freedom to rotate about the rotation axis A1, extending in the vertical direction, rotate about a rotation axis A2 extending in the vertical direction, and rotate about a rotation axis A3 extending in the vertical direction. Further, with the vertical articulated assembly 23, the robotic arm 2 has three degrees of freedom to rotate about a rotation axis B1 extending a horizontal direction, rotate about a rotation axis B2 extending in the horizontal direction, and rotate about a rotation axis B3 extending in the horizontal direction. Furthermore, with the pitch mechanism 24, the robotic arm 2 has one degree of freedom to allow the table 1 to pitch about a rotation axis extending in the transverse direction of the table 1 (Y direction).

Figure 3:
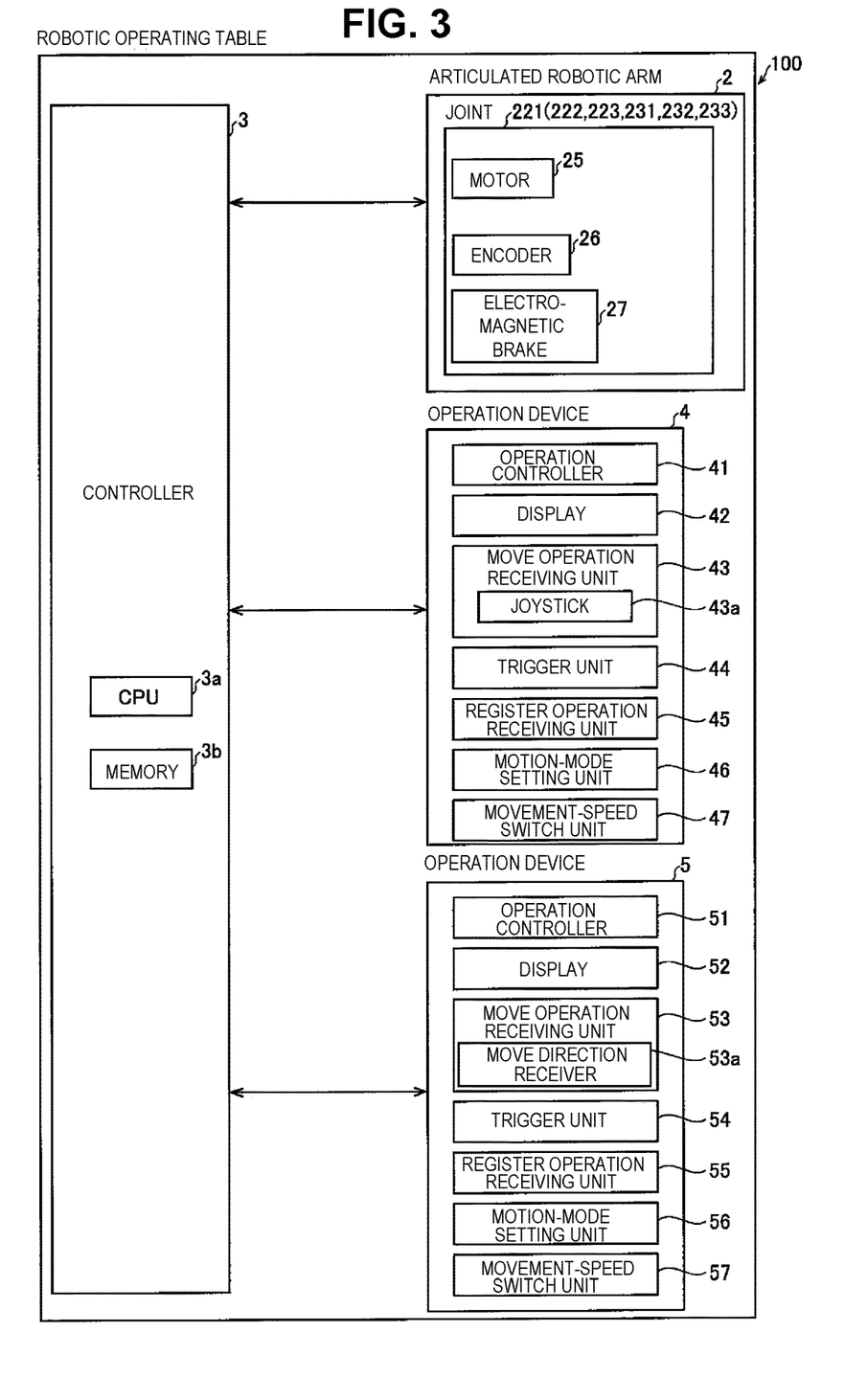
FIG. 3 is a block diagram illustrating the control configuration of a robotic operating table according to one or more embodiments.

As illustrated in FIG. 3, the joints of the robotic arm 2 (horizontal joints 221 to 223 and vertical joints 231 to 233) each include a motor 25, an encoder 26, an electromagnetic brake 27, and a reducer (not illustrated). The motor 25 is a drive source for the joint to rotate the table 10. The motor 25 includes a servomotor. Also, the motor 25 is driven based on control by the controller 3. The encoder 26 measures the amount of rotation of the motor 25. Also, the encoder 26 transmits the result of the measurement of the amount of rotation of the motor 25 to the controller 3. The controller 3 acquires position information on the table 1, posture information on the table 1, and posture information on the robotic arm 2 based on the result of the measurement by the encoder 26. The electromagnetic brake 27 is a negative actuated-type electromagnetic brake that stops the rotation by the motor 25. Specifically, the electromagnetic brake 27 cancels braking of the motor 25 when the motor 25 is energized, and brakes the motor 25 when the motor 25 is de-energized. The electromagnetic brake 27 may be an electromagnetic brake incorporated in the motor 25 or an electromagnetic brake externally mounted to the motor 25.

Also, the robotic arm 2 causes the table 1 to yaw about an axis extending in the vertical direction (Z direction) by using at least one of the horizontal joints (at least one of 221, 222, and 223). Further, the robotic arm 2 causes the table 1 to roll about an axis extending in the longitudinal direction (X direction) by using at least one of the vertical joints (at least one of 231, 232, and 233). Furthermore, the robotic arm 2 causes the table 1 to pitch about an axis extending in the transverse direction (Y direction) by using the pitch mechanism 24.

The controller 3 is control circuitry including, for example, a CPU (Central Processing Unit) 3a and a memory 3b. The memory 3b according to one or more embodiments may include such devices as a flash memory device, magnetic disk device such as a hard disk drive, and an optical disk device that reads data from a recording medium. In one or more embodiments, for example, the recording medium may include Blu-ray disk, CD-ROM (Compact Disk Read Only Memory), DVD (Digital Versatile Disk). The controller 3 is disposed inside the base 21 and controls movement of the table 1 by the robotic arm 2. Specifically, the controller 3 moves the table 1 by controlling the motion of the robotic arm 2 based on an operation input by a medical person (user).

Figure 4:
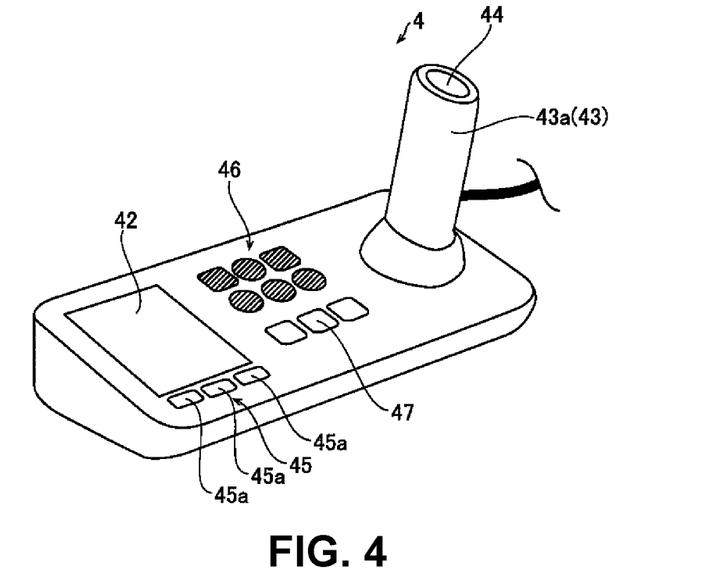
FIG. 4 is a perspective view illustrating an operation device including a joystick of a robotic operating table according to one or more embodiments.
Figure 5:
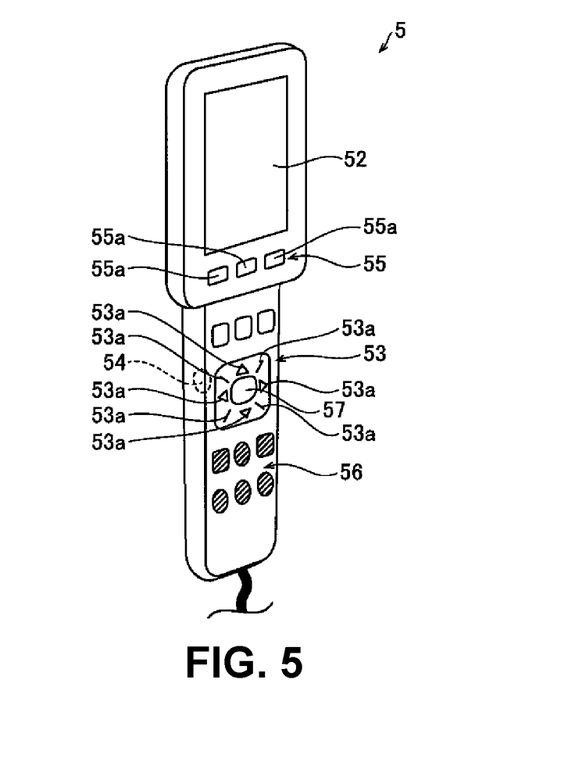
FIG. 5 is a perspective view illustrating an operation device with move direction receivers of a robotic operating table according to one or more embodiments.

As illustrated in FIG. 3 to FIG. 5, the operation device 4 and the operation device 5 receive operations input by a medical person (user) for moving the table 1. The operation devices 4 and 5 are each capable of receiving operations for the table 1. The operation device 4 is an operation device mainly used while mounted to the table 1. The operation device 5 is an operation device mainly used from a position away from the table 1. The operation devices 4 and 5 are detachably mounted to the table 1 by being engaged with engagement portions (not illustrated) provided on a side surface of the support part 12 of the table 1. The operation devices 4 and 5 are connected to the controller 3 so as to be capable of making wired communication with the controller 3.

As illustrated in FIG. 3 and FIG. 4, the operation device 4 includes an operation controller 41, a display 42, a move operation receiving unit 43, a trigger unit 44, a register operation receiving unit 45, a motion-mode setting unit 46, and a movement-speed switch unit 47. As illustrated in FIG. 3 and FIG. 5, the operation device 5 includes an operation controller 51, a display 52, a move operation receiving unit 53, a trigger unit 54, a register operation receiving unit 55, a motion-mode setting unit 56, and a movement-speed switch unit 57.

The operation controller 41 (51) controls units in the operation device 4 (5) based on operations input by a medical person (user). For example, the operation controller 41 (51) controls imagery to be displayed on the display 42 (52) based on an operation input by the medical person (user). Moreover, the operation controller 41 (51) transmits operation information indicating an operation input by the medical person (user) to the controller 3. The controller 3 performs control that causes the robotic arm 2 to move the table 1 based on the received operation information.

The display 42 (52) displays the state of the table 1, the state of operation on the operation device 4 (5), an operation screen, and so on. The display 42 (52) includes a display, such as liquid crystal display or an organic EL (Electro Luminescence) display. Meanwhile, in the operating room 200, the controller 3 of the robotic operating table 100, the operation controller 41 (51), and the display 400 (see FIG. 1) are communicatively connected to each other, and the display 400 is capable of displaying the state of the table 1, the state of operation on the operation device 4 (5), the operation screen, and so on. The display 400 is capable of displaying, for example, an image displayed on the display 42 (52) of the operation device 4 (5). In this way, multiple medical persons in the operating room 200 can check the state of operation on the robotic operating table 100 at the same time. Also, the display 400 can be a touchscreen-type input and display and may receive an operation input by a medical person (user) for moving the table 1 through an operation on a screen.

The move operation receiving unit 43 (53) receives a move operation to move the table 1 from a medical person (user). The move operation receiving unit 43 of the operation device 4 includes a joystick 43a. The joystick 43a is operated by being tilted. Moreover, the joystick 43a receives an operation for moving the table 1 that reflects the direction of the tilt and the angle of the tilt. The move operation receiving unit 53 of the operation device 5 includes multiple (eight) move direction receivers 53a provided respectively for directions in which to move the table 1. In other words, the move direction receivers 53a are provided for eight directions. Each of the move direction receivers 53a receives an operation for moving the table 1 by being pressed. Meanwhile, the eight move direction receivers 53a are capable of lighting up using incorporated light sources formed of light emitting diodes.

The trigger unit 44 (54) is provided to enable operations on the move operation receiving unit 43 (53). Specifically, the trigger unit 44 (54) has a function to allow energization of the motors 25 by being operated. The controller 3 performs control that energizes the motors 25 while the trigger unit 44 (54) is operated. Thus, operating the trigger unit 44 (54) cancels braking of the motors 25 by the electromagnetic brakes 27. Hence, operations on the move operation receiving unit 43 (53) are enabled and the table 1 can be moved only while the trigger unit 44 (54) is operated. On the other hand, in the robotic operating table 100, the motors 25 are de-energized when the operation on the trigger unit 44 (54) is canceled. The controller 3 actuates the electromagnetic brakes 27 by stopping the energization of the motors 25 when the trigger unit 44 (54) is not operated. Thus, cancelling the operation on the trigger unit 44 (54) causes the electromagnetic brakes 27 to brake the motors 25. Hence, any operations on the move operation receiving unit 43 (53) are disabled and the table 1 cannot be moved when the trigger unit 44 (54) is not operated.

The trigger unit 44 of the operation device 4 is provided at the tip of the joystick 43a. Pressing the trigger unit 44 of the operation device 4 enables operations on the joystick 43a. On the other hand, any operations on the joystick 43a are disabled in the state where the pressing of the trigger unit 44 is canceled. The trigger unit 54 of the operation device 5 is provided at the surface opposite from the surface where the move direction receivers 53a are provided. Pressing the trigger unit 54 of the operation device 5 enables operations on the move direction receivers 53a. On the other hand, any operations on the move direction receivers 53a are disabled in the state where the pressing of the trigger unit 54 is canceled.

The register operation receiving unit 45 (55) receives, from the user, a register operation and a set operation for a to-be-registered or registered position as the position a movement destination of the table 1. The register operation receiving unit 45 (55) includes multiple (three) register operation receiving buttons 45a (55a). The register operation receiving unit 45 (55) receives a register operation and a set operation for a to-be-registered or registered position with each register operation receiving button 45a (55a). In other words, the robotic operating table 100 is capable of registering multiple different to-be-registered positions. The register operation receiving unit 45 (55) receives a registration operation or a setting operation for a to-be-registered or registered position when a register operation receiving button 45a (55a) is pressed.

Figure 6:
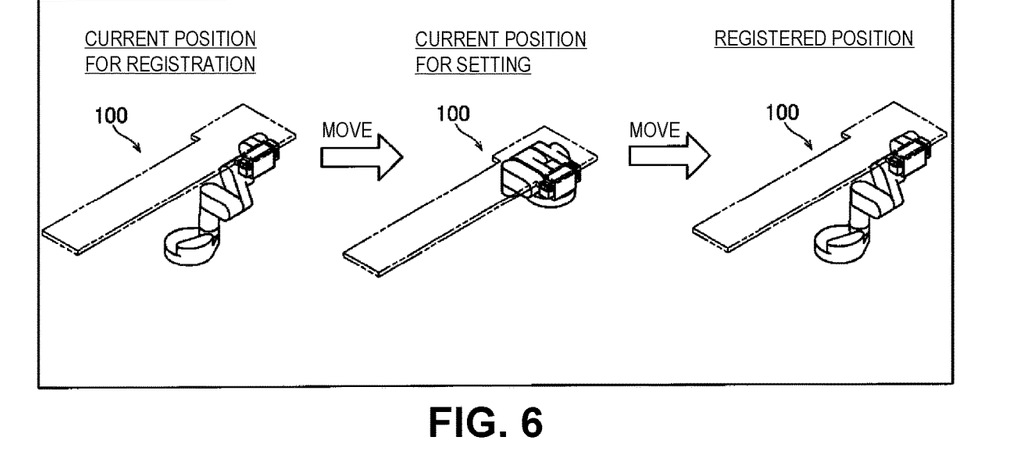
FIG. 6 is a diagram illustrating control for registering a to-be-registered position, control for setting the registered position, and control for moving to the registered position by a robotic operating table according to one or more embodiments.

Here, in one or more embodiments, as illustrated in FIG. 6, when the register operation receiving unit 45 (55) receives a register operation, the controller 3 causes the position of the table 1 at the current position for registration, as a registered position, and the posture of the robotic arm 2 at the current position for registration to be stored in the memory 3b. Specifically, when a register operation receiving button 45a (55a) of the register operation receiving unit 45 (55) is operated, the controller 3 causes the position of the table 1 and the posture of the robotic arm 2 at the current position to be stored in the memory 3b.

Also, when the register operation receiving unit 45 (55) receives a set operation, the controller 3 sets the corresponding registered position as the movement destination of the table 1. Specifically, when a register operation receiving button 45a (55a) of the register operation receiving unit 45 (55) is operated, the controller 3 sets the corresponding registered position stored in the memory 3b as the movement destination of the table 1.

Then, when the move operation receiving unit 43 (53) receives a move operation with the registered position set as the movement destination of the table 1, the controller 3 controls the motion of the robotic arm 2 such that the table 1 will be placed at the registered position with the position of the table 1 and the posture of the robotic arm 2 stored in the memory 3b. In other words, the controller 3 performs control that causes the robotic arm 2 to move the table 1 from the current position for setting toward the registered position such that the table 1 will be placed at the registered position with the position of the table 1 and the posture of the robotic arm 2 stored in the memory 3b.

Also, in one or more embodiments, the controller 3 performs control that causes the robotic arm 2 to move the table 1 while the move operation receiving unit 43 (53) is receiving a move operation.

Specifically, if the operation device 4 is receiving an operation input by a medical person (user), the controller 3 performs control that causes the robotic arm 2 to move the table 1 toward a registered position while the joystick 43a is operated with the registered position set as the movement destination of the table 1. In other words, if the operation device 4 is receiving an operation input by a medical person (user), the table 1 is moved toward a registered position only while the joystick 43a is operated.

Further, if the operation device 5 is receiving an operation input by a medical person (user), the controller 3 performs control that causes the robotic arm 2 to move the table 1 toward a registered position while one of the move direction receivers 53a is operated with the registered position set as the movement destination of the table 1. In other words, if the operation device 5 is receiving an operation input by a medical person (user), the table 1 is moved toward a registered position only while a move direction receiver 53a is operated.

Furthermore, if one of the operation devices 4 and 5 is receiving an operation input by a medical person (user), the controller 3 performs control that causes the robotic arm 2 to move the table 1 toward a registered position while the trigger unit 44 (54) and the move operation receiving unit 43 (53) are simultaneously operated with the registered position set as the movement destination. In other words, if the operation device 4 is receiving an operation input by a medical person (user), the table 1 is moved only while an operation of pressing the trigger unit 44 and an operation of tilting the joystick 43a are performed simultaneously. Also, if the operation device 5 is receiving an operation input by a medical person (user), the table 1 is moved only while an operation of pressing the trigger unit 54 and an operation of pressing a move direction receiver 53a are performed simultaneously.

Also, in one or more embodiments, when the table 1 is placed at the registered position with the position of the table 1, the posture of the table 1, and the posture of the robotic arm 2 stored in the memory 3b, the controller 3 performs control that disables the operation on the move operation receiving unit 43 (53) to thereby stop the movement of the table 1. Then, when the user stops operating the trigger unit 44 (54), the controller 3 stops the energization of (de-energizes) the motors 25 in the joints of the robotic arm 2 (horizontal joints 221 to 223 and vertical joints 231 to 233) to thereby actuate the electromagnetic brakes 27 in the joints. In other words, the controller 3 performs control that stops the energization of (de-energizes) the motors 25 in the joints of the robotic arm 2 to thereby actuate the electromagnetic brakes 27 in the joints when the trigger unit 44 (54) is not pressed in the state where the table 1 is placed at the registered position with the position of the table 1, the posture of the table 1, and the posture of the robotic arm 2 stored in the memory 3b.

As illustrated in FIG. 3 to FIG. 5, the motion-mode setting unit 46 (56) is provided to set one motion mode among multiple motion modes defined in advance. The motion-mode setting unit 46 (56) receives a operation to set a motion mode from the user. The multiple motion modes include, for example: a yaw mode in which the table 1 is rotated in a horizontal plane about a rotation axis extending in the vertical direction (Z direction); a horizontal movement mode in which the table 1 is linearly moved in a horizontal plane; an elevation mode in which the table 1 is raised or lowered; a roll mode in which the table 1 is rotated about an axis extending in parallel to the longitudinal direction of the table 1 (X direction); and a pitch mode in which the table 1 is rotated about an axis extending in parallel to the transverse direction of the table 1 (Y direction). In the yaw mode, the table 1 is caused to yaw based on an operation input by a medical person (user). In the horizontal movement mode, the table 1 is linearly moved based on an operation input by a medical person (user). In the elevation mode, the table 1 is moved in the vertical direction (Z direction) based on an operation input by a medical person (user). In the roll mode, the table 1 is caused to roll based on an operation input by a medical person (user). In the pitch mode, the table 1 is caused to pitch based on an operation input by a medical person (user). The user sets a motion mode among the multiple motion modes based on the desired motion by using the motion-mode setting unit 46 (56). In the robotic operating table 100, the table 1 is moved when the trigger unit 44 (54) and the move operation receiving unit 43 (53) are operated with a motion mode selected using the motion-mode setting unit 46 (56).

The movement-speed switch unit 47 (57) receives a operation to change the movement speed of the table 1 from the user. Also, the movement-speed switch unit 47 (57) receives an operation for changing the movement speed of the table 1 by being pressed. The robotic operating table 100 changes the movement speed of the table 1 to a different level of movement speed each time the movement-speed switch unit 47 (57) is pressed. For example, the movement speed of the table 1 can be changed through three levels of movement speed.

(Configuration of Radiographic Imaging Apparatus)

The configuration of the radiographic imaging apparatus 300 is explained with reference to FIG. 1.

As illustrated in FIG. 1, the radiographic imaging apparatus 300 is capable of capturing a radiographic projection image of the patient 10 placed on the table 1 of the robotic operating table 100. The radiographic imaging apparatus 300 includes an X-ray irradiation part 301, an X-ray detection part 302, and a C-arm 303. The X-ray irradiation part 301 and the X-ray detection part 302 are supported on the C-arm 303. The X-ray irradiation part 301 and the X-ray detection part 302 are moved with movement of the C-arm 303, and are positioned to face each other from opposite sides of the patient 10 during imaging of the patient 10 using X rays. For example, one of the X-ray irradiation part 301 and the X-ray detection part 302 is positioned in a space above the table 1 while the other is positioned in a space under the table 1. Also, during imaging of the patient 10 using X rays, the C-arm 303, supporting the X-ray irradiation part 301 and the X-ray detection part 302, is partly positioned in the spaces above and under the table 1 as well.

The X-ray irradiation part 301 is disposed to face the X-ray detection part 302. Also, the X-ray irradiation part 301 is capable of emitting X rays toward the X-ray detection part 302. The X-ray detection part 302 detects the X rays emitted by the X-ray irradiation part 301. The X-ray detection part 302 includes an FPD (Flat Panel Detector). The X-ray detection part 302 converts the detected X rays into electric signals and transmits them to an image processing unit (not illustrated).

The X-ray irradiation part 301 is connected to one end of the C-arm 303, and the X-ray detection part 302 is connected to the opposite end of the C-arm 303. The C-arm 303 has a substantially C-shape. In this way, the C-arm 303 can support the X-ray irradiation part 301 and the X-ray detection part 302 in such a position that the table 1 and the patient 10 are situated therebetween, during imaging of the patient 10 using X rays. The C-arm 303 is capable of moving relative to the table 1. Specifically, the C-arm 303 is capable of moving horizontally and vertically and also rotating about a horizontal rotation axis and a vertical rotation axis. In this way, the X-ray irradiation part 301 and the X-ray detection part 302 can be placed at a desired position relative to the patient 10 placed on the table 1. The C-arm 303 is moved by a drive part (not illustrated) based on an operation input by a medical person (user). The C-arm 303 is also manually movable by a medical person (user). Meanwhile, the radiographic imaging apparatus 300 and the display 400 are communicatively connected to each other. The display 400 is capable of displaying radiographic fluoroscopic images captured by the radiographic imaging apparatus 300 and a radiographic image captured by the radiographic imaging apparatus 300.

(Registration Process)

Next, a registration process for registering a to-be-registered position by the robotic operating table 100 of one or more embodiments is explained with reference to a flowchart in FIG. 7.

Figure 7:
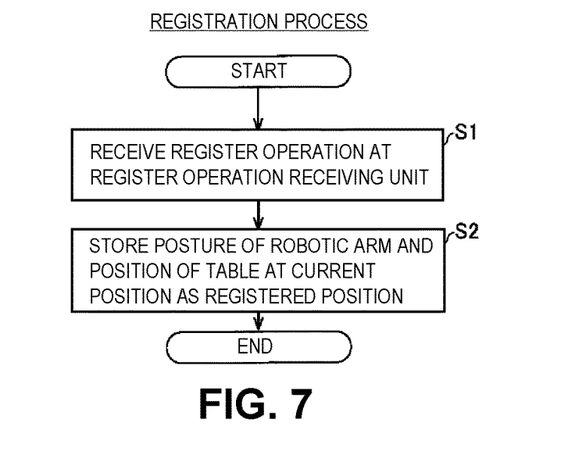
FIG. 7 is a flowchart illustrating a registration process by a robotic operating table according to one or more embodiments.

As illustrated in FIG. 7, first in step S1, the register operation receiving unit 45 (55) of the operation device 4 (5) receives a register operation from a medical person (user).

Then in step S2, the controller 3 causes the position of the table 1 and the posture of the robotic arm 2 at the current position for registration to be stored in the memory 3b. As a result, a to-be-registered position is registered. The registration process is then terminated.

(Setting Process)

Next, a setting process for setting a registered position by the robotic operating table 100 of one or more embodiments is explained with reference to a flowchart in FIG. 8.

Figure 8:
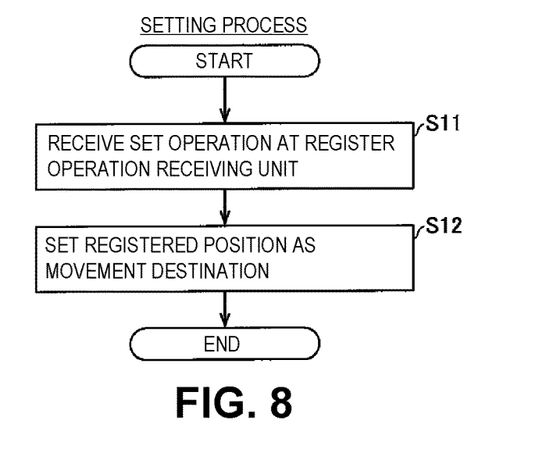
FIG. 8 is a flowchart illustrating a setting process by a robotic operating table according to one or more embodiments.

As illustrated in FIG. 8, first in step S11, the register operation receiving unit 45 (55) of the operation device 4 (5) receives a set operation from a medical person (user).

Then in step S12, the controller 3 performs control that sets a registered position as the movement destination from the current position for setting. The setting process is then terminated.

(Movement Process)

Next, a movement process for moving to a registered position by the robotic operating table 100 of one or more embodiments is explained with reference to a flowchart in FIG. 9.

Figure 9:
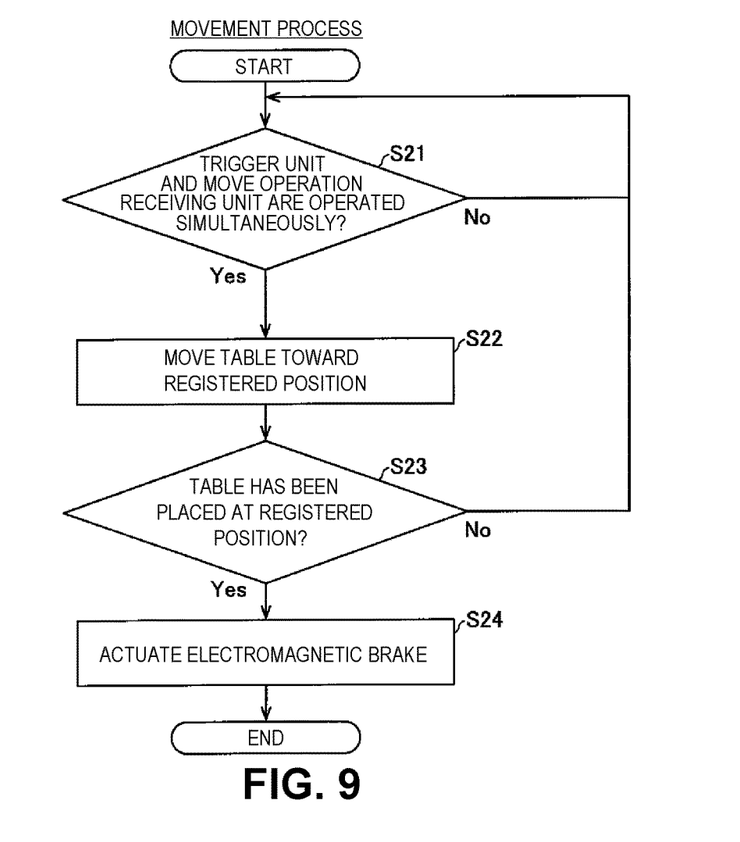
FIG. 9 is a flowchart illustrating a movement process by a robotic operating table according to one or more embodiments.

As illustrated in FIG. 9, first in step S21, it is determined whether or not the trigger unit 44 (54) and the move operation receiving unit 43 (53) of the operation device 4 (5) are being operated simultaneously.

The process of step S21 is repeated if it is determined in step S21 that the trigger unit 44 (54) and the move operation receiving unit 43 (53) are not being operated simultaneously.

If the trigger unit 44 (54) is not being operated in step S21, the motors 25 in the joints of the robotic arm 2 (horizontal joints 221 to 223 and vertical joints 231 to 233) are in the de-energized state and the electromagnetic brakes 27 are therefore braking the motors 25 in the joints, so that the table 1 does not move. Also, if the trigger unit 44 (54) is being operated but the move operation receiving unit 43 (53) is not being operated in step S21, the move operation receiving unit 43 (53) is not receiving any move operation from a medical person (user). The motors 25 are therefore not driven, so that the table 1 does not move.

On the other hand, if it is determined in step S21 that the trigger unit 44 (54) and the move operation receiving unit 43 (53) are being operated simultaneously, the process proceeds to step S22.

Then in step S22, the controller 3 performs control that causes the robotic arm 2 to move the table 1 toward the registered position set in the setting process.

Then in step S23, it is determined whether or not the table 1 has been placed at the registered position. In other words, it is determined whether or not the table 1 and the robotic arm 2 have been placed with the position of the table 1 and the posture of the robotic arm 2 stored in the memory 3b. If it is determined that the table 1 has not yet been placed at the registered position, the process returns to step S21. Then, the processes of step S21 to step S23 are repeated. In other words, in step S21 to step S23, the controller 3 performs control that causes the robotic arm 2 to move the table 1 toward the registered position only while the trigger unit 44 (54) and the move operation receiving unit 43 (53) are operated simultaneously.

On the other hand, if it is determined in step S23 that the table 1 has been placed at the registered position, the controller 3 disables the operation on the move operation receiving unit 43 (53) to thereby stop the movement, and the process proceeds to step S24. Meanwhile, in doing so, the controller 3 may notify the user that the table 1 has reached the registered position.

Then in step S24, the user stops operating the trigger unit 44 (54), thereby stopping the energization of the motors 25 in the joints of the robotic arm 2 and thus actuating the electromagnetic brakes 27 in the joints. The movement process is then terminated. Note that even if the move operation receiving unit 43 (53) is being operated in step S24, the energization of the motors 25 in the joints of the robotic arm 2 is stopped and the electromagnetic brakes 27 in the joints are thus actuated.

ADVANTAGEOUS EFFECTS OF ONE OR MORE EMBODIMENTS

One or more embodiments can offer the following advantageous effects.

In one or more embodiments, as explained above, when the register operation receiving unit 45 (55) receives a register operation, the controller 3 causes the registered position and the posture of the robotic arm 2 to be stored in the memory 3b. Then, the controller 3 controls the motion of the robotic arm 2 such that the table 1 will be placed at the registered position with the posture of the robotic arm 2 stored in the memory 3b, when the move operation receiving unit 43 (53) receives a move operation in the state where the register operation receiving unit 45 (55) has received a set operation and the registered position has been set as the movement destination of the table 1. In this way, the table 1 with the patient 10 placed thereon can be moved back to a registered position at which the table 1 was positioned a little while ago, with a simple operation. Also, the robotic arm 2 is provided, which includes one end supported on the base and the opposite end supporting the table 1. In this way, the table 1 can be moved by the robotic arm 2 with a large freedom of movement. Hence, the table 1, on which to place the patient 10, can have a large range and freedom of movement. As a result of these, the table 1, on which to place the patient 10, can have a large range and freedom of movement and also the table 1 with the patient 10 placed thereon can be moved back to a registered position at which the table 1 was positioned a little while ago, with a simple operation. Also, since the table 1, on which to place the patient 10, can have a large range and freedom of movement, the table 1 can be moved to various positions (patient receiving position, anesthetization position, surgical operation position, imaging position, and so on) desired by medical persons such as surgeons, assistants, nurses, and medical technicians. In addition, it is possible to prevent a situation where the range of movement of the table 1 is small such that sufficient space cannot be left around the positions at which the medical persons stand. Accordingly, surgery can be performed more easily.

Also, in the case of moving the table 1 by means of the robotic arm 2, if the table 1 is moved back to a position at which the table 1 was positioned a little while ago without taking the posture of the robotic arm 2 into account, the robotic arm 2 may be placed in a different posture from the original posture at the position to which the table 1 is moved back. In this case, the robotic arm 2 may become an obstacle at the position to which the table 1 is moved back. To solve this, the robotic operating table 100 according to one or more embodiments stores a registered position and the posture of the robotic arm 2 in the memory 3b and controls the motion of the robotic arm 2 such that the table 1 will be placed at the registered position with the posture of the robotic arm 2 stored in the memory 3b, as explained above. In this way, in the case of moving the table 1 by means of the robotic arm 2 too, the robotic arm 2 will be placed in the original posture at the position at which the table 1 is moved back. Hence, the robotic arm 2 can be prevented from becoming an obstacle at the position at which the table 1 is moved back.

Also, in one or more embodiments, as explained above, the robotic arm 2 includes joints (horizontal joints 221 to 223 and vertical joints 231 to 233). Moreover, each of the joints of the robotic arm 2 includes a motor 25, an encoder 26, and an electromagnetic brake 27. Furthermore, the controller 3 performs control that places the table 1 at a registered position with the posture of the robotic arm 2 stored in the memory 3b, and stops energization of the motors 25 in the joints to thereby actuate the electromagnetic brakes 27 in the joints when the user stops operating the trigger unit 44 (54). In this way, the electromagnetic brakes 27 can be actuated at the registered position. Hence, the table 1 can be reliably stopped at the registered position.

Also, in one or more embodiments, as explained above, the register operation receiving unit 45 (55) includes the register operation receiving buttons 45a (55a). Moreover, when a register operation receiving button 45a (55a) is operated, the controller 3 causes a registered position and the posture of the robotic arm 2 to be stored in the memory 3b. In this way, the posture of the memory 3b can be stored as a registered position simply by operating a register operation receiving button 45a (55a). Hence, a to-be-registered position can be registered with a simple operation.

Also, in one or more embodiments, as explained above, when a register operation receiving button 45a (55a) is operated, the controller 3 sets the corresponding registered position as the movement destination of the table 1. In this way, the movement destination of the table 1 can be set to a registered position simply by operating a register operation receiving button 45a (55a). Hence, a registered position can be set with a simple operation. Also, since the registration of a to-be-registered position and the setting of the registered position can be done by using the same button, the registration of a to-be-registered position and the setting of the registered position can be done with a simple and intuitive operation.

Also, in one or more embodiments, as explained above, the controller 3 performs control that causes the robotic arm 2 to move the table 1 while the move operation receiving unit 43 (53) is receiving a move operation. In this way, the table 1 is not moved while the move operation receiving unit 43 (53) is not receiving a move operation. Hence, if even the move operation receiving unit 43 (53) operated unintentionally, the table 1 can be prevented from continuing to be moved unintentionally. Also, in the case of moving the table 1 intentionally too, the movement of the table 1 can be stopped simply by stopping operating the move operation receiving unit 43 (53). Hence, when the table 1 that is being moved is desired to be stopped from being moved, the movement of the table 1 can be stopped easily and quickly.

Also, in one or more embodiments, as explained above, the move operation receiving unit 53 includes the move direction receivers 53a, which are provided respectively for directions in which to the table 1. Moreover, the controller 3 performs control that causes the robotic arm 2 to move the table 1 toward a registered position while one of the move direction receivers 53a is operated with the registered position set as the movement destination of the table 1. In this way, the table 1 can be moved toward a registered position only by operating one of the move direction receivers 53a. Hence, the table 1 can be moved toward a registered position with a simple operation. Also, the table 1 is not moved while none of the move direction receivers 53a is operated. In this way, the table 1 can be prevented from continuing to be moved unintentionally. Also, in the case of moving the table 1 toward a registered position by operating the move direction receivers 53a, if the table 1 that is being moved is desired to be stopped from being moved, the movement of the table 1 can be stopped easily and quickly.

Also, in one or more embodiments, as explained above, the move operation receiving unit 43 includes the joystick 43a. Moreover, the controller 3 performs control that moves causes the robotic arm 2 to move the table 1 toward a registered position while the joystick 43a is operated with the registered position set as the movement destination of the table 1. In this way, the table 1 can be moved toward a registered position only by operating the joystick 43a. Hence, the table 1 can be moved toward a registered position with a simple operation. Also, the table 1 is not moved while the joystick 43a is not operated. In this way, the table 1 can be prevented from continuing to be moved unintentionally. Also, in the case of moving the table 1 toward a registered position by operating the joystick 43a, if the table 1 that is being moved is desired to be stopped from being moved, the movement of the table 1 can be stopped easily and quickly.

Also, in one or more embodiments, as explained above, the operation device 4 (5) includes the trigger unit 44 (54), which enables operations on the move operation receiving unit 43 (53). Moreover, the controller 3 performs control that causes the robotic arm 2 to move the table 1 toward a registered position while the trigger unit 44 (54) and the move operation receiving unit 43 (53) are operated with the registered position set as the movement destination of the table 1. In this way, the table 1 is moved only while both the trigger unit 44 (54) and the move operation receiving unit 43 (53) are operated. Hence, the table 1 can be prevented from being moved unintentionally when the move operation receiving unit 43 (53) is operated unintentionally.

Also, in one or more embodiments, as explained above, the operation device 4 (5) includes the trigger unit 44 (54). Moreover, the robotic arm 2 includes joints (horizontal joints 221 to 223 and vertical joints 231 to 233). Further, each of the joints includes a motor 25 and a negative actuated-type electromagnetic brake 27. Furthermore, the controller 3 performs control that stops energization of the motor 25 to thereby actuate the electromagnetic brake 27 while the trigger unit 44 (54) is not operated, and energizes the motor 25 while the trigger unit 44 (54) is operated. In this way, the table 1 is not moved while the trigger unit 44 (54) is not moved. Hence, the table 1 can be prevented from being moved unintentionally when the move operation receiving unit 43 (53) is operated unintentionally.

Also, in one or more embodiments, as explained above, the one end of the robotic arm 2 is supported on the base 21 to be rotatable about an axis extending in the vertical direction. Also, the opposite end of the robotic arm 2 supports the table 1 at a position near its one end in the longitudinal direction of the table 1. Furthermore, the robotic arm 2 moves the table 1 with seven degrees of freedom. In this way, the table 1, on which to place the patient 10, can have a large range and freedom of movement as compared to cases where the robotic arm 2 moves the table 1 with six or fewer degrees of freedom. Moreover, with the robotic arm 2 moving the table 1 with seven degrees of freedom, the table 1 can be easily moved to desired positions.

Also, in one or more embodiments, as explained above, the table 1 includes the radiolucent part 11 and the support part 12, disposed on the one end side of the table 1 in the longitudinal direction of the table 1 and supporting the radiolucent part 11. Moreover, the opposite end of the robotic arm 2 supports the support part 12. In this way, it is possible to minimize the portion of the robotic arm 2 disposed around the radiolucent part 11. Hence, it is possible to leave a sufficient space to place the radiographic imaging apparatus 300 around the radiolucent part 11.

(Modifications)

Note that one or more embodiments disclosed this time should be considered exemplary in all aspects and not limiting. The scope of the present invention is indicated by the claims rather than the explanation of the above one or more embodiments and also embraces all changes that come within the meaning and range of equivalents of the claims.

For example, although the example in which a radiographic imaging apparatus is provided in a hybrid operating room has been presented in the above, the present invention is not limited to this example. In one or more embodiments, a magnetic resonance imaging apparatus that captures a magnetic resonance image of a patient may be provided in a hybrid operating room. Also, both a radiographic imaging apparatus and a magnetic resonance imaging apparatus may be provided in a hybrid operating room.

Also, although the example in which the robotic operating table is provided in a hybrid operating room has been presented in the above, the present invention is not limited to this example. In one or more embodiments, the robotic operating table may be provided in an operating room other than a hybrid operating room.

Also, although the example in which the robotic operating table is provided with two operation devices has been presented in the above, the present invention is not limited to this example. In one or more embodiments, the robotic operating table may be provided with one operation device or provided with three or more operation devices.

Also, although the example in which the operation devices are connected to the controller so as to be capable of making wired communication with the controller has been presented in the above, the present invention is not limited to this example. For example, the operation devices may be connected to the controller so as to be capable of making wireless communication with the controller.

Also, although the example in which registered positions are stored in the memory included in the controller has been presented in the above, the present invention is not limited to this example. For example, registered positions may be stored in memories included in the operation devices, or registered positions may be stored in a separate memory provided independently of the controller and the operation devices.

Also, although the example in which the move direction receivers are provided for eight directions has been presented in the above, the present invention is not limited to this example. In one or more embodiments, the move direction receivers may be provided for multiple directions other than eight directions.

Also, although the example in which each register operation receiving unit includes three register operation receiving buttons has been presented in the above, the present invention is not limited to this example. In one or more embodiments, each register operation receiving unit may include one or two register operation receiving buttons or include four or more register operation receiving buttons.

Figure 10:
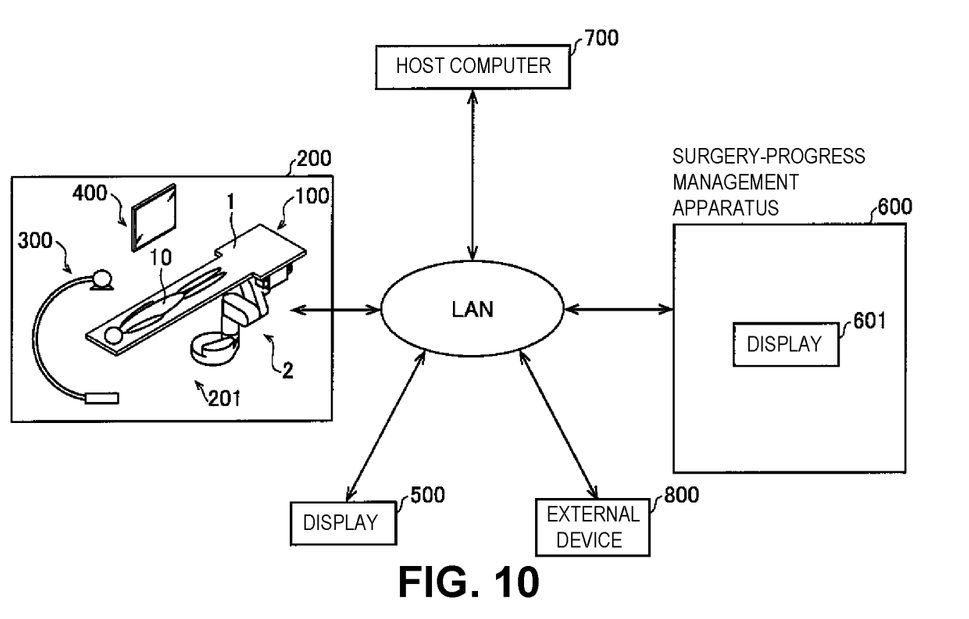
FIG. 10 is a diagram illustrating displays according to a modification of one or more embodiments.

Also, although the example in which the state of the table, the state of operation on each operation device, the operation screen, and so on are displayed on the display provided inside the operating room in addition to the display of the operation device has been presented in the above, the present invention is not limited to this example. For example, as in a modification illustrated in FIG. 10, the state of the table, the state of operation on each operation device, the operation screen, and so on may be displayed on a display provided outside the operating room. Specifically, as illustrated in FIG. 10, the state of the table and so on may be displayed on a display 500 provided outside the operating room 200 and connected to an LAN (Local Area Network) inside the hospital in which the operating room 200 is provided. The display 500 is provided in, for example, a nurses' station. Also, in a case where a surgery-progress management apparatus 600 that manages the progress of surgery is provided outside the operating room 200, the state of the table and so on may be displayed on a display 601 of the surgery-progress management apparatus 600. The display 601 of the surgery-progress management apparatus 600 is provided in, for example, a control center next to the operating room 200. Meanwhile, a host computer 700, an external device 800 such as a mobile terminal which a hospital official has, and so on may be connected to the LAN inside the hospital.

Also, although the example in which the horizontal articulated assembly includes three horizontal joints has been presented in the above, the present invention is not limited to this example. In one or more embodiments, the horizontal articulated assembly may include two horizontal joints or include four or more horizontal joints.

Also, although the example in which the vertical articulated assembly includes three vertical joints has been presented in the above, the present invention is not limited to this example. In one or more embodiments, the vertical articulated assembly may include two vertical joints or include four or more vertical joints.

Also, although the example in which the articulated robotic arm is provided with a series of three horizontal joints and a series of three vertical joints has been presented in the above, the present invention is not limited to this example. In one or more embodiments, for example, a vertical articulated robot with portions at each of which joints adjacent to each other have their rotation axes arranged perpendicular to each other, may be used as the articulated robotic arm.

Also, although the example in which the articulated robotic arm has seven degrees of freedom has been presented in the above, the present invention is not limited to this example. In one or more embodiments, the articulated robotic arm may have six or fewer degrees of freedom or have eight or more degrees of freedom. However, it is preferable for the robotic arm to have six or more degrees of freedom.

Also, although the example in which the base is buried in and fixed to the floor has been presented in the above, the present invention is not limited to this example. In one or more embodiments, the base may be fixed to the surface of the floor.

Also, although the example in which the controller is disposed inside the base has been presented in the above, the present invention is not limited to this example. In one or more embodiments, a control box with the controller housed in a casing may be provided. For example, the control box may be disposed at any position inside the operating room or the control box may be disposed in the control center next to the operating room.

Also, in the above, the example with the configuration has been presented in which the controller performs control that, when the table reaches a registered position, disables the operation on the move operation receiving unit to thereby stop the movement of the table and, when the user stops operating the trigger unit, stops the energization of the motors to thereby actuate the electromagnetic brakes. However, the present invention is not limited to this example. For example, when the table reaches a registered position, the controller may stop the energization of the motors to thereby actuate the electromagnetic brakes even if the move operation receiving unit and the trigger unit are still operated simultaneously.

The invention claimed is:

1. A robotic operating table comprising:
a table on which to place a patient;
a robotic arm comprising a plurality of joints, and having a first end supported on a base fixed to a floor, and a second end supporting the table;
an operation device comprising:
a move operation receiving unit that comprises a first input device that is to be operated by a user and receives a move operation to move the table, and
a register operation receiving unit that comprises a second input device that is to be operated by the user and receives a register operation to register a position of a movement destination of the table and a movement-destination set operation;
a memory; and
a controller that causes the robotic arm to move the table based on the move operation received by the move operation receiving unit, wherein
when the register operation receiving unit receives the register operation, the controller causes a position of the table at a point in time when the register operation receiving unit receives the register operation to be stored as a registered position in the memory and causes a posture of the robotic arm at the point in time when the register operation receiving unit receives the register operation to be stored associated with the registered position of the table in the memory,
the move operation receiving unit comprises move direction receivers provided respectively for directions in which to move the table, and
in a condition in which the registered position is set as the movement destination of the table, the controller causes the robotic arm to move the table toward the registered position in response to any one of the move direction receivers being operated even when the direction of the operated move direction receiver is different than the direction in which the table moves toward the registered position.

2. The robotic operating table according to claim 1, wherein
each of the plurality of joints of the robotic arm comprises a motor, an encoder, and an electromagnetic brake, and
the robotic arm, after placing the table at the registered position, fixes the posture of the robotic arm by stopping energization of the motor in each of the plurality of joints and actuating the electromagnetic brake in each of the plurality of joints.

3. The robotic operating table according to claim 1, wherein
the register operation receiving unit comprises a register operation receiving button, and
the controller causes the registered position and the posture of the robotic arm to be stored in the memory when the register operation receiving button is operated.

4. The robotic operating table according to claim 3, wherein when the register operation receiving button is operated after the register operation is received via the register operation receiving button, the controller sets the registered position as the movement destination of the table.

5. The robotic operating table according to claim 1, wherein the controller causes the robotic arm to move the table while the move operation receiving unit is receiving the move operation.

6. The robotic operating table according to claim 1, wherein
the move operation receiving unit comprises a joystick, and
the controller causes the robotic arm to move the table toward the registered position while the joystick is operated in any direction with the registered position set as the movement destination of the table.

7. The robotic operating table according to claim 1, wherein
the operation device comprises a trigger unit that comprises a third input device that is to be operated by the user and enables an operation on the move operation receiving unit, and
the controller causes the robotic arm to move the table toward the registered position only while both the trigger unit and the move operation receiving unit are simultaneously operated by the user with the registered position set as the movement destination of the table, and the controller does not cause the robotic arm to move the table toward the registered position while both of the trigger unit and the move operation receiving unit are not simultaneously operated by the user with the registered position set as the movement destination of the table.

8. The robotic operating table according to claim 1, wherein
the operation device comprises a trigger unit,
each of the plurality of joints comprises a motor and an electromagnetic brake,
the controller, while the trigger unit is not operated, performs control that stops energization of the motor and actuates the electromagnetic brake, and
the controller, while the trigger unit is operated, performs control that energizes the motor.

9. The robotic operating table according to claim 1, wherein
the first end of the robotic arm is supported on the base to be rotatable about an axis extending in a vertical direction,
the second end of the robotic arm supports the table at a position near an end of the table in a longitudinal direction, and
the robotic arm moves the table with at least six degrees of freedom.

10. The robotic operating table according to claim 1, wherein
the table comprises:
a radiolucent part; and
a support part provided on an end of the table in a longitudinal direction of the table and supporting the radiolucent part, and
the second end of the robotic arm supports the support part.

11. The robotic operating table according to claim 1, wherein
in the condition in which the registered position is set as the movement destination of the table, only while said any one of the move direction receivers is operated, the controller controls the robotic arm to move the table toward the registered position.

12. A robotic operating table comprising:
a table on which to place a patient;
a robotic arm comprising a plurality of joints, and having a first end supported on a base fixed to a floor, and a second end supporting the table;
an operation device that receives operations from a user;
a memory; and
a controller causes the robotic arm to move the table based on a move operation received by the operation device, wherein
when the operation device receives a register operation, the controller causes a position of the table at a point in time when the operation device receives the register operation to be stored as a registered position in the memory and causes a posture of the robotic arm at the point in time when the operation device receives the register operation to be stored associated with the registered position of the table in the memory,
the operation device comprises a joystick to move the table, and
in a condition in which the registered position is set as a movement destination of the table, the controller causes the robotic arm to move the table toward the registered position in response to the joystick being operated in any direction even when the direction in which the joystick is operated is different than the direction in which the table moves toward the registered position.

13. The robotic operating table according to claim 12, wherein
each of the plurality of joints of the robotic arm comprises a motor, an encoder, and an electromagnetic brake, and
the robotic arm, after placing the table at the registered position, fixes the posture of the robotic arm by stopping energization of the motor in each of the plurality of joints and actuating the electromagnetic brake in each of the plurality of joints.

14. The robotic operating table according to claim 12, wherein
the operation device comprises a trigger unit,
each of the plurality of joints comprises a motor and an electromagnetic brake,
the controller, while the trigger unit is not operated, performs control that stops energization of the motor and actuates the electromagnetic brake, and
the controller, while the trigger unit is operated, performs control that energizes the motor and does not actuate the electromagnetic brake.

15. The robotic operating table according to claim 12, wherein
the operation device comprises:
a move operation receiving unit that receives the move operation, and
a trigger unit that enables an operation on the move operation receiving unit, and
the controller causes the robotic arm to move the table while the trigger unit and the move operation receiving unit are operated.

16. The robotic operating table according to claim 15, wherein the controller does not cause the robotic arm to move the table in a condition in which the move operation receiving unit is operated and the trigger unit is not operated.

17. The robotic operating table according to claim 15, wherein the controller does not cause the robotic arm to move the table in a condition in which the trigger unit is operated and the move operation receiving unit is not operated.

18. The robotic operating table according to claim 12, wherein
the first end of the robotic arm is supported on the base to be rotatable about an axis extending in a vertical direction,
the second end of the robotic arm supports the table at a position near an end of the table in a longitudinal direction, and
the robotic arm moves the table with at least six degrees of freedom.

19. The robotic operating table according to claim 12, wherein
the table comprises:
a radiolucent part; and
a support part provided on an end of the table in a longitudinal direction of the table and supporting the radiolucent part, and
the second end of the robotic arm supports the support part.

20. The robotic operating table according to claim 12, wherein
in the condition in which the registered position is set as the movement destination of the table, only while the joystick is operated, the controller controls the robotic arm to move the table toward the registered position.

21. A hybrid operation system comprising:
a robotic operating table; and
at least one of a radiographic imaging apparatus configured to capture a radiographic projection image of a patient and a magnetic resonance imaging apparatus configured to capture a magnetic resonance image of a patient;
wherein the robotic operating table comprises:
a table on which to place a patient;
a robotic arm comprising a plurality of joints, and having a first end supported on a base fixed to a floor, and a second end supporting the table;
an operation device that receives an operation from a user;
a memory; and
a controller that causes the robotic arm to move the table based on a move operation received by the operation device, wherein
when the operation device receives a register operation, the controller causes a position of the table at a point in time when the operation device receives the register operation to be stored as a registered position in the memory and causes a posture of the robotic arm at the point in time when the operation device receives the register operation to be stored associated with the registered position of the table in the memory,
the operation device comprises move direction receivers provided respectively for directions in which to move the table, and
in a condition in which the registered position is set as a movement destination of the table, the controller causes the robotic arm to move the table toward the registered position in response to any one of the move direction receivers being operated even when the direction of the operated move direction receiver is different than the direction in which the table moves toward the registered position.

22. The hybrid operation system according to claim 21, wherein
in the condition in which the registered position is set as the movement destination of the table, only while said any one of the move direction receivers is operated, the controller controls the robotic arm to move the table toward the registered position.

* * * * *